US00PP09885P

United States Patent [19]

Bessho et al.

[11] Patent Number: Plant 9,885

[45] Date of Patent: May 6, 1997

[54] PETUNIA PLANT NAMED 'LIRICASHOWER BLUE'

[75] Inventors: Masao Bessho; Seiji Nakamura, both of Kakegawa; Hitoshi Kojima, Kikukawa-machi, all of Japan

[73] Assignee: Sakata Seed Corporation, Yokohama, Japan

[21] Appl. No.: 585,887

[22] Filed: Jan. 16, 1996

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—James R. Cypher

[57] ABSTRACT

Disclosed herein is a new and distinct decumbent type Petunia plant named 'Liricashower Blue', having compact growth habit bred from crosses made in Japan from South America commercial Petunias of creeping growth habit. The new variety is strongly branching with a great profusion of blooms. The flowers are single and small with violet blue colored petals. The plant is highly resistant to rain, heat, and drought.

2 Drawing Sheets

BACKGROUND

This invention relates to a new and distinct cultivar of Petunia plant, hereinafter referred to by the name 'Liricashower Blue'. 'Liricashower Blue' Petunia originated from a hybridization made in 1991 by the inventors Masao Bessho, Seiji Nakamura, Hitoshi Kojima at Sakata Seed Corporation, Kakegawa breeding station in Kakegawa, Japan. The female parent was a clear purple red, creeping habit plant with breeder code 701-1 and the male parent was a bright purple red, creeping habit plant with breeder code 1C-1. Both parents originated from the commercial markets in South America. The crosses (breeder code $F_1$) were pollinated in the early spring of 1992 to obtain breeder code $F_2$ seed. The resulting $F_2$ seeds were sown in the summer of 1992 and produced 60 plants for selection. Selections were made for better creeping and branching habit and subsequently vegetatively propagated by cutting. The primary asexual propagation occurred in 1992. In 1993, cuttings from the plants were field grown for further selection of desired traits. Again in 1994, the cuttings of selected plants were field grown for final selection and evaluation for stability of desired traits. These asexual reproductions, of the final selection, by cuttings and field grown trial planting were performed at the Sakata Seed America, Inc. research station at Salinas, Calif., and the Sakata Seed Corporation breeding station in Kakegawa, Japan under the direction and supervision of the inventors. The invention, 'Liricashower Blue' Petunia, after three years of successive vegetative propagation by cuttings was determined by the inventors to have its combination of characteristics as herein described firmly fixed.

'Liricashower Blue' is a new variety of Petunia plant having a decumbent and compact habit. The plant has abundant branching and a large profusion of blooms and makes an excellent presentation in hanging baskets. The flowers are single, small in size (3.0 cm) and petals are a violet blue color (R.H.S. 88A). The plant is very resistant to rain, heat, and drought. The plant grows and flowers best under low soil pH conditions (5–6 pH). Typically, young flowers will close under low light and low temperature conditions such as conditions late in the day and at night.

The new cultivar is distinguished from any other Petunia plants of which we are aware by its violet blue color, and excellent creeping-branching habit and large profusion of blooms making it a particularly desirable plant for hanging basket arrangements.

The closest commercial cultivar to my new variety of which I am aware is the Petunia plant named 'Million Bell Blue'. The distinguishing characteristics which are outstanding in the new cultivar and which distinguish it from 'Million Bell Blue' are:

| | 'Liricashower Blue' | 'Million Bell Blue' |
|---|---|---|
| Habit | Creeping Vigorous Growth | Erect Compact Growth |
| Flower Size | 3.0 cm | Smaller |
| Flower Color | Bright Violet Blue | Light Purple |
| Flower Throat Color | Light Green Yellow | Bright Green Yellow |

BRIEF DESCRIPTION OF DRAWINGS

The accompanying drawings serve by color photographic means to illustrate the new plant variety, 'Liricashower Blue'. The colors are represented as true as possible using conventional photographic procedures.

Figure 1:
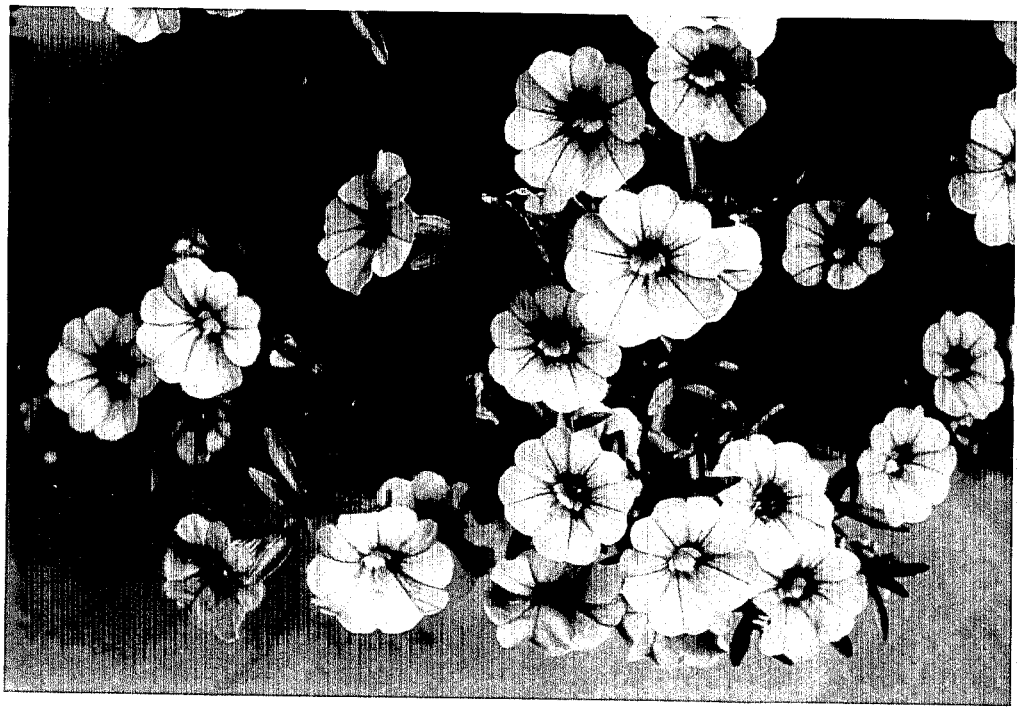
FIG. 1 is a close-up view of multiple blooms illustrating the decumbent, compact habit; abundant branching; and large profusion of blooms.
Figure 2:
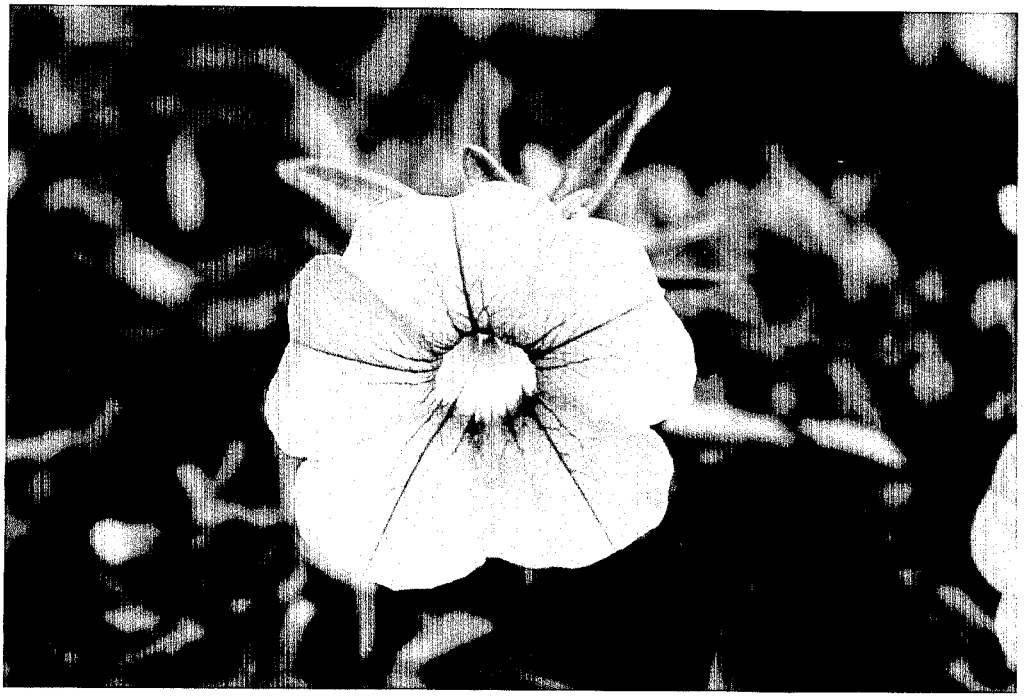
FIG. 2 is a close-up view of a single bloom.
Figure 3:
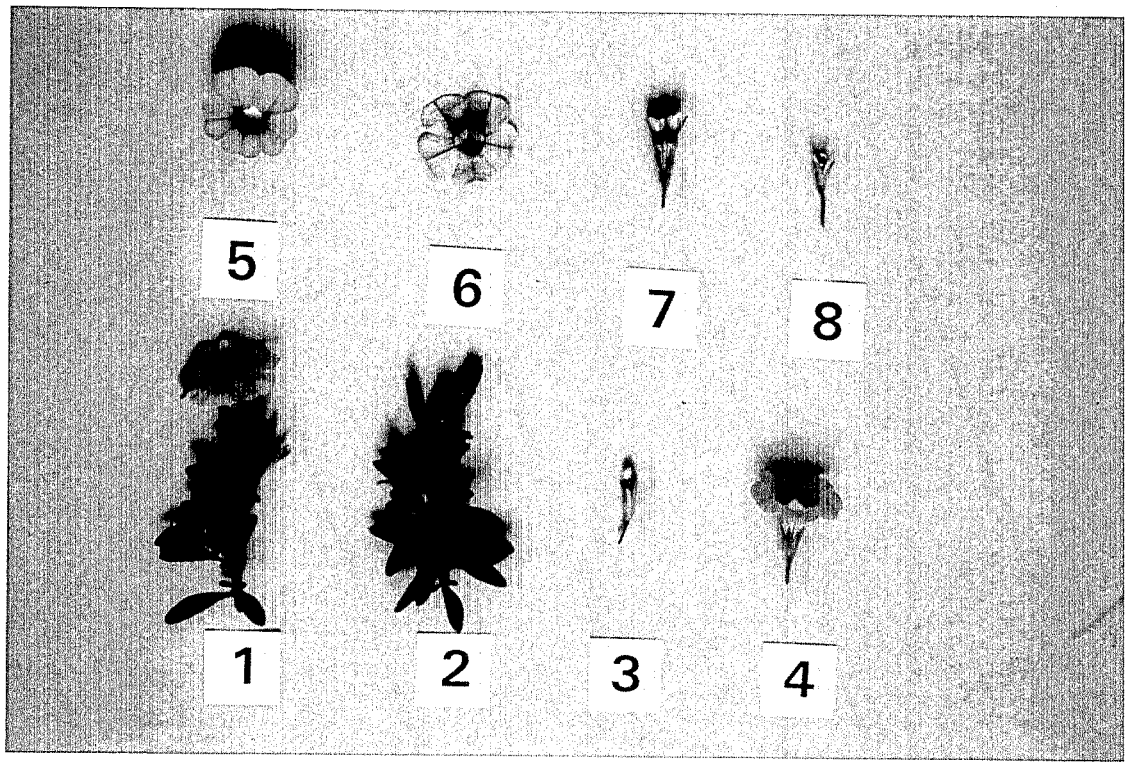
FIG. 3 is a view of the new cultivar in various stages of flower development.

1. full bloom with stem
2. bud with stem
3. small bud (unopened)
4. side view of flower in full bloom
5. front view of the flower in full bloom
6. rear view of flower in full bloom
7. side view of partially opened flower
8. pistil and stamens of full bloom flower stage

DETAILED DESCRIPTION OF THE NEW VARIETY

The following description is based on observations and measurements of pot grown plants in Salinas, Calif. Color designations were made according to The Royal Horticultural Society Colour Chart published by The Royal Horticultural Society of London, England.

PLANT

Origin: Seedling.

Parentage:

*Female parent.*—Unpatented and unnamed commercial market plant from South America, breeder Code 701-1.

*Male parent.*—Unpatented and unnamed commercial market plant from South America, breeder code 1C-1.

Classification:

*Family.*—Solanaceae.

*Genius.*—Petunia.

*Botanical.*—Unknown; Petunia species.

*Commercial.*—Petunia 'Liricashower Blue'.

Growth habit: Decumbent.

Plant height: 5–7 cm, will mound on itself.

Spreading area of the plant: Stems extend to a length of 40–50 cm for a spreading area of 80–100 cm (in a 4 inch pot).

Growth: Vigorous growth with excellent basal branching and a profusion of continuous flowers.

Blooming period: Continuously under moderate temperatures of 15–25 degrees centigrade.

Resistance: Excellent resistance to rain, heat and drought.

Stem:

*Thickness.*—Main stem 2–2.5 mm; laterals 1–1.5 mm.

*Color.*—Dull yellow green R.H.S. 146B with anthocyanin present on the axial portion of the stem.

*Pubescence.*—Slight.

*Branching.*—Abundant.

*Length of internode.*—4 mm at base of stem to 2 cm near tips of stems.

Leaf:

*Phyllotaxis.*—Verticillate.

*Leaf attaching angle.*—Primarily vertical.

*Shape.*—Slightly oblanceolate and entire.

*Shape of tip.*—Acute.

*Size (average).*—9 mm long and 2 mm wide on smallest leaf in the whorl, 2.5 cm long and 6 mm wide on largest in the whorl.

*Thickness.*—0.5 mm–0.8 mm.

*Color.*—Medium dark green R.H.S. 147B.

*Pubescence.*—Slight.

Flowers:

*Quantity.*—Abundant.

*Type.*—Opens obliquely upward, single.

*Shape.*—Funnel shape, with 5 fissured limb, a gamopetalous corolla, slight indent on each petal.

*Shape of tip.*—Retuse.

*Lobation.*—None.

*Undulation of margin.*—None.

*Diameter.*—2.5 cm–3.0 cm when fully open.

*Color.*—Unopened stage: grayish violet R.H.S. 90C with darker venation 90A on upper 3 petals, no venation on the lower 2 petals.

*Full bloom.*—Opened; violet R.H.S. 88A and fading slightly with age to 88B, throat showing pale white to cream to light green yellow tones.

*Reproductive organs.*—One pistil, five stamens, 2 with long filaments bending upward over the pistil and 3 short filaments, anther is yellow, filaments are white.

*Peduncle.*—Length is 1.5 mm on fully opened flowers, 0.6 mm on young flowers.

We claim:

1. A new and distinct cultivar of Petunia plant named 'Liricashower Blue', as herein illustrated and described.

* * * * *